United States Patent [19]

Narayanan

[11] Patent Number: 5,435,939
[45] Date of Patent: * Jul. 25, 1995

[54] STABLE EMULSIFIABLE GEL MATRIX AND AQUEOUS MACROEMULSION PREPARED THEREFROM

[75] Inventor: Kolazi S. Narayanan, Palisades Park, N.J.

[73] Assignee: ISP Investments Inc., Wilmington, Del.

[*] Notice: The portion of the term of this patent subsequent to Apr. 5, 2011 has been disclaimed.

[21] Appl. No.: 89,070

[22] Filed: Jul. 7, 1993

[51] Int. Cl.$^6$ ............ A01N 25/04; A01N 25/30; B01J 13/00

[52] U.S. Cl. .......... 252/312; 71/DIG. 1; 252/311; 252/315.3; 252/363.5; 424/409; 424/418; 514/941; 514/944; 514/965

[58] Field of Search ............ 252/311, 312, 315.3; 514/941, 944, 965; 424/409, 418; 71/DIG. 1

[56] References Cited

U.S. PATENT DOCUMENTS

| | | | |
|---|---|---|---|
| 4,002,456 | 1/1977 | Maas | 71/DIG. 1 |
| 4,007,258 | 2/1977 | Cohen et al. | 424/418 |
| 4,502,975 | 3/1985 | Kobayashi et al. | 252/315.1 |
| 4,762,718 | 8/1988 | Marks, Sr. | 424/409 |
| 5,002,938 | 3/1991 | Wang et al. | 514/944 |
| 5,071,463 | 12/1991 | Narayanan et al. | 71/DIG. 1 |
| 5,139,152 | 8/1992 | Hodakowski et al. | 71/DIG. 1 |
| 5,266,590 | 11/1993 | Narayanan | 514/938 |
| 5,283,229 | 2/1994 | Narayanan et al. | 71/DIG. 1 |
| 5,294,644 | 3/1994 | Login et al. | 71/DIG. 1 |
| 5,317,042 | 5/1994 | Narayanan | 514/937 |

*Primary Examiner*—Richard D. Lovering
*Attorney, Agent, or Firm*—Walter Katz; Marilyn J. Maue; Joshua J. Ward

[57] ABSTRACT

What is provided herein is a stable, emulsifiable gel matrix for an agriculturally active chemical, which matrix will form an emulsifiable gel concentrate upon addition of the agriculturally active chemical, and upon water dilution, a highly stable aqueous macroemulsion which avoids precipitation of the active ingredient on extended storage. In addition, the inventive emulsifiable gel concentrates may contain relatively high concentrations of the agriculturally active chemical, the concentration sometimes referred herein to as "loading", making it advantageous from both the economic and handling viewpoints.

11 Claims, No Drawings

STABLE EMULSIFIABLE GEL MATRIX AND AQUEOUS MACROEMULSION PREPARED THEREFROM

BACKGROUND OF THE INVENTION

1. Field of the Invention

The invention relates to a delivery system for agriculturally active chemicals, and more particularly, the invention relates to a stable emulsifiable gel matrix for difficult to dissolve agricultural chemicals, an emulsifiable gel concentrate with said agricultural chemical, and an aqueous macroemulsion of said concentrate with dilution water.

2. Description of the Prior Art

Agricultural chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into an emulsion, it is difficult to maintain the emulsified state. This makes it difficult to maintain a uniform formulation, particularly, when the formulation is diluted with water for application to the plants.

Typically, for example, an agriculturally active ingredient is mixed with one or more of a variety of conventional solvents and an emulsifying agent to form an emulsifiable concentrate. This concentrate may be in the form of an emulsion, suspension, or solution. The concentrate is then stored until it is transported to the site of use or may simply be transported and stored at the site of use. In any event, the concentrate normally will undergo some period of storage until it is ready for use. Understandably, it is most desirable to be able to transport the agriculturally active ingredient at the highest concentration possible so as to minimize the volume of material which need be transported. By the same token, however, at the use site, it is normally not feasible to admix ingredients together or to process them other than to dilute the concentrate with water. Accordingly, it is important that the concentrate emulsify easily, i e, exhibit good "bloom", upon the addition of water. In addition, at the use site, it is often necessary to store the diluted concentrate for extended time periods until the actual application to the plants. Consequently, it is important that the diluted form of the concentrate exhibit good stability with respect to the uniformity of the emulsion and to avoid precipitation of the active ingredients. If non-uniformity or precipitation occurs in the diluted form, then non-uniformity will result in the application of the diluted formulation to the plants.

Substantial progress in providing emulsifiable concentrates which avoid the problems of the prior art are disclosed in U.S. Pat. No. 5,071,463, the contents of which are incorporated herein by reference. The emulsifiable concentrates of these disclosures all require the presence of a hydrophobic solvent having the following Hansens' solubility parameters: Dispersive component from about 56 to 75%; Polar component from about 8 to 24%; and H-bonding component of from about 10 to 30%.

This second component should also have surfactant properties and act as a non-ionic surfactant with an HLB value ranging from about 2 to 8. Examples of this solvent or component include alkylpyrrolidones having an alkyl portion containing from 6 to 14 carbon atoms, e.g., octylpyrrolidone, dodecylpyrrolidone, or N-(2'-ethylhexylpyrrolidone), alkyl gamma-butyrolactones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. For each of the above examples, the 6 to 14 carbon alkyl portions may be straight, branched, or cyclic, with straight chains being preferred. The preferred component or hydrophobic solvent is indicated as being long chain alkyl, and particularly those selected from pyrrolidones having the formula

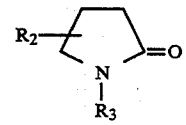

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14.

Accordingly, it is an object of this invention to provide a stable, emulsifiable gel matrix for an agriculturally active chemical.

Another object of this invention is to provide an emulsifiable gel concentrate upon addition of the agriculturally active chemical to the gel matrix.

Still another object herein is to provide a stable, aqueous macroemulsion upon dilution of the concentrate with water.

A particular object of the invention is to provide a stable, emulsifiable gel matrix and concentrate which can be readily dispersed in dilution water to form the aqueous macroemulsion.

These and other objects of the invention will be made apprent from the following description of the invention.

SUMMARY OF THE INVENTION

What is provided herein is a stable, emulsifiable gel matrix for an agriculturally active chemical, which matrix will form an emulsifiable gel concentrate upon addition of the agriculturally active chemical, and upon water dilution, a highly stable aqueous macroemulsion which avoids precipitation of the active ingredient on extended storage. In addition, the inventive emulsifiable gel concentrates may contain relatively high concentrations of the agriculturally active chemical, the concentration sometimes referred herein to as "loading", making it advantageous from both the economic and handling viewpoints.

More particularly, the stable emulsifiable gel matrix of the present invention is composed of a surfactant to provide both dispersing and wetting functions for the agriculturally active chemical, a solvent system composed of a first lactam component having a sufficiently high hydrophilic property to solubilize the agriculturally active chemical, and a second lactam component which is a hydrophobic solvent, and mixtures thereof, and a thickening agent, a high molecular weight polymer to function as either a viscosity enhancer or a disintegration aid, or both, for the gel concentrate; optionally including an organic diluent and a polyhydric alcohol.

A preferred gel matrix for forming a gel for concentrate a herbicide, insecticide or fungicide as the agricultural chemical, includes an anionic or nonionic surfactant, a $C_1$-$C_4$ alkylpyrrolidone as the solubilizing first lactam solvent, a $C_6$-$C_{18}$ alkylpyrrolidone as the hydrophobic second lactam solvent, a hydroxy alkyl cellulose as the thickening agent, and a high molecular weight polyvinylpyrrolidone, or vinylpyrrolidone copolymer, or maleic acid ester-alkyl vinyl ether copolymer as the viscosity enhancer and/or disintegration aid.

Preferably the stable gel concentrate of the invention has a viscosity of $\geq 5,000$ cps.

Upon dilution of the gel concentrate with water, an aqueous macroemulsion is formed which can be applied directly to plants.

DETAILED DESCRIPTION OF THE INVENTION

The first lactam component of the solvent system of the gel matrix has a high hydrophilic property which is particularly suitable for forming a stable, emulsifiable gel matrix and concentrate. Typical examples include alkylpyrrolidones having from 1 to 4 carbon atoms in the alkyl group. Mixtures of these may also be used as the first component.

Accordingly, the first lactam component of the solvent system is selected from the group consisting of pyrrolidones having the formula

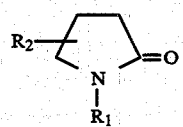

wherein R is hydrogen or lower alkyl having from 1 to 4 carbon atoms and $R_1$ is lower alkyl having from 1 to 4 carbon atoms. A preferred compound is N-methylpyrrolidone.

Examples of appropriate hydrophobic lactam solvents in the emulsifiable gel matrix and concentrate herein include alkylpyrrolidones having an alkyl portion containing from 6 to 18 carbon atoms, e.g., octylpyrrolidone, iso-octylpyrrolidone, dodecylpyrrolidone, or N-(2′-ethylhexylpyrrolidone), and mixtures thereof, wherein the alkyl chains contain from 6 to 18 carbon atoms. The alkyl portion may be distributed at one or more sites on the ring so long as one portion contains at least 6 carbon atoms and the total number of alkyl carbon atoms does not exceed 18. Preferred 6 to 18 carbon alkyl portions are composed of straight chains. Branched or cyclic alkyl portions may also be used.

Accordingly, the hydrophobic lactam solvent is preferably selected from pyrrolidones having the formula

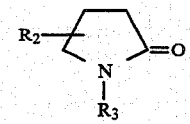

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 18.

The inventive gel matrix also contains a surfactant which is generally selected on a case by case basis in order to optimize the solubility and stability of the emulsion. Anionic and nonionic surfactants are preferred. Typically, such surfactants include ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines. Anionic surfactants include phosphate esters and their salts, alkyl sulfonamides, salts of sulfated nonylphenoxypoly(ethyleneoxy) ethanol, salts of alkylbenzene sulfonates, also of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and Detergent* (1989), published by McCutcheon's Division of M.C. Publishing Co., Glen Rock, N.J.)

Representative nonionic surfactants include:

Alkylphenol ethoxylated alcohol having an HLB $\geq 6$, e.g., nonylphenol ethoxylated alcohol with 9 EOs—(Igepal ® CO-630); and Ethylene oxide (EO)/propylene oxide (PO)/EO block copolymers, e.g., (2 EO/16 PO12 EO-H$_2$O—(-Pegale ® L-31).

Representative anionic surfactant include nonylphenol ethoxylated phosphate esters with 9 EOs—(-Gafac ® RE-610).

The emulsifiable gel matrix of the invention also includes a thickening agent such as a hydroxy alkyl cellulose, e.g. Klucel ®, to provide a matrix having a viscosity of about 700–10,000 cps.

Another essential component of the emulsifiable gel matrix is a viscosity enhancer and/or a disintegration aid, suitably a high molecular weight polymer, e.g. polyvinylpyrrolidone, a vinylpyrrolidone-alkene copolymer, e.g. Ganex ® (ISP), or a half-ester (methyl-ethyl or butyl) of maleic anhydride and an alkyl vinyl ether copolymer, e.g. Gantrez ® (ISP).

The emulsifiable gel matrix also may include optionally a polyhydric alcohol, such as glycerol.

The inventive gel matrix optionally may include an organic diluent which suitably is a synthetic or naturally occurring oil having a high hydrophobic character or having a fractional dispersive solubility parameter of greater than 70% and preferably greater than 85% and a molar volume of greater than 90 cm³/mole.

These properties are defined in the C.R.C. Handbook referred to hereinabove. Typical diluents include soybean oil, rapeseed oil, long chain alcohols, long chain ketones, long chain esters, and ethers. As used herein, "long chain" means with 6 or more carbon atoms. Also suitable as the organic diluent are aromatic petroleum oils including those which are commercially available distillates from crude oils having an average boiling point greater than 200° C. Typical of such materials are those sold under the trademarks Exxon 200 or Texaco 400. Of course, such aromatic petroleum oils should be approved for use as a carrier for agriculturally active chemicals.

The composition of the aromatic petroleum oil is generally:

Heavy aromatic solvent naphtha—about 60%;
Middle distillate solvent extractant—about 40%.

Normally, these oils contain predominantly the $C_9$–$C_{15}$ aromatic hydrocarbons and primarily the $C_{10}$–$C_{12}$ hydrocarbons having a flash point of about 203° F.

The agriculturally active chemical then is added to the matrix to form the gel concentrate. The concentration of the chemical should be as high as possible so long as it does not precipitate out upon dilution of the concentrate with water for a reasonable period of time and achieves the desired effect. Precipitation (crystal formation) on standing not only depletes the solution of chemical, it can also lead to fouling of application equipment, i.e., sprayers, etc. With the present invention, it is possible to obtain concentrates with agriculturally active chemical concentrations in excess of about 5 weight percent which form a stable emulsion upon being diluted with water. Preferably, the amount of chemical is from 5 to 30% and, most preferably, 10 to 20%. As used herein, all percents are percents by weight based on the total weight of the composition, unless otherwise specified.

AS used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or animals or domestic uses for controlling insects and pests. Particularly, such chemicals would normally take the form of water-immiscible or oily liquids and/or solids which is substantially insoluble in water. By the term "substantially insoluble", it is meant that for all practical purposes, the solubility of the compound in water is insufficient to make the compound practicably usable in an agricultural end use without some modifications either to increase its solubility or dispersability in water, so as to increase the compound's bioavailability or avoid the use of excessively large volumes of solvent.

Agricultural chemicals normally take the form of water-immiscible or oily liquids and/or solids. Suitable agriculturally active chemicals which can be used with the present invention include insecticides, herbicides and fungicides. Typical insecticides include cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W. T. Thomson, Thomson Publications.) Typical of the insecticides are:

| | |
|---|---|
| cyclocompounds: | 6,7,8,9,10,10-hexachloro-1,5,5a,6,9,9a-hexahydro-6,9-methano-2,4,3-benzodioxathiepin-3-oxide benzo-diooxathiepin-3-oxide |
| carbamates: | 2-isopropyl phenyl-N-methyl carbamate; |
| | 2-(1,3-dioxolan-2yl) phenylmethyl carbamate; |
| | 2,3-isopropylidine dioxyphenyl methyl carbamate; |
| animal and plant derivatives: | chlorinated hydrocarbons derived from Southern pine; naturally occurring lactone glycoside; |
| synthetic pyrethroids: | (±) alpha-cyano-3-phenoxybenzyl (±) cis, trans 3-(2,2-dichlorovinyl)-2,2-dimethyl cyclopropane carboxylate; |
| | (±) cyano (3-phenoxyphenyl methyl (±)-4-(difluoromethyoxy) alpha-(1-methylethyl) benzene acetate; |
| | D-allethrin |
| | permethrin |
| | tetramethrin |
| | cypermethrin |
| | piperonyl butoxide (synergist) |
| phenoxy compounds and non-phosphate: | 2,2-bis(p-methoxy phenyl)-1,1,1,trichloroethane; 1,3,5,tri-n-propyl-1,3,5-triazine-2,4,6 (1H,3H,5H) trione; |
| | ethyl (2E, 4E)-3,7,11-trimethyl- 2,4-dodeca dienoate: |
| | 1-decycloxy 4-[(7-oxa-oct-4-ynyl)]-oxybenzene; |
| organic phosphates: | dimethyl phosphate ester of 3-hydroxy-N,N-dimethyl-cis-crotonamide; |
| | 2-chloro-1-(2,4-dichloro phenyl) vinyl diethylphosphate; |
| | 4-(methyl thio) phenyl dipropyl phosphate; |
| thiophosphates: | 0,0-diethyl-0-4-nitrophenyl phosphorothioate; |
| | 0,0-diethyl-0-(2,isopropyl-6- methyl-5-pyrimidinyl) phosphorothioate; |
| | 2-diethylamino-6-methyl pyrimidine-4-yl dimethyl phosphorothioate; |
| dithiophosphates: | 0,0-dimethyl phosphorodithioate ester of diethylmercapto succinate; |
| | 0-ethyl-S-phenyl ethyl phosphorodithioate. |

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g. triazines, pyridines, pyridazones, picolinic acid, and urea derivates and phosphates. (See *Agricultural Chemicals*, Book II, *Herbicides*, 1986-87 Edition, W. T. Thomson, Thomson Publications, Fresno, Calif. 93791.) Exemplary of the above compounds are:

| | |
|---|---|
| phenoxy compounds: | 2,4-Dichlorophenoxy acetic acid |
| | 2,4,5-trichloro phenoxyacetic acid; |
| | 4-(2,4-dichlorophenoxy) butyric acid; |
| | S-ethyl 2 methyl-4-chlorophenoxy-thioacetate; |
| | 2-methyl-4-chloro-phenoxy acetic acid; |
| | methyl 5-(2,4-dichloro-phenoxy)-2-nitrobenzoate; |

| | |
|---|---|
| benzoic and acetic acids of phthalic compounds: | 3,6-dichloro-o-anisic acid 4-chloro-2-oxo benzothiazolin-3-yl acetic acid; N-1-Naphthyl-phthalamic acid; |
| nitriles and aniline derivatives: | 3-5-dibromo-4-hydroxybenzonitrile; α,α,α,trifluoro-2,6-dinitro-N,N-dipropyl-p-tolinidine; N-(1-ethylpropyl)-2,6-dinitro-3,4-xylidine; |
| amides, acetamides, anilides: | N,N-diethyl-2-(1-naphthalenyl oxy)-propionamide; 2,6-dimethyl-N-2' methoxy-ethyl-chloro-acetanilide; 3',4'-dichloro-propionanilide; α-chloracetic-N-(3,5,5-trimethyl-cyclohexen-1-yl)-N-isopropylamide; 4-benzyl-N-isopropyl trimethyl acetamide; |
| thiocarbamates: | S-Ethyl dipropyl thiocarbanate; |
| urea derivatives: | 3-(5-tert-butyl-3-isoxazoyl)-1,1-dimethyl urea; N-(2,6-trifluoro-benzoyl)-N'-[2,5-dichloro-4-(1,1,2,3,3,3-hexafluoropropyloxy) phenyl] urea; |
| pyrrolidone derivatives: | 1-(m-trifluoro methyl phenyl)-3-chloro-4-chloromethyl-2-pyrrolidone; |
| amino acid derivatives: | methyl N-benzoyl-N-(3-chloro-4-fluorophenyl)-DL alarinate; N-chloroacetyl-N-(2,6-diethyl phenyl)-glycine ethyl ester; |
| carbamates: | Isopropyl-m-chlorocarbanilate; 3-Ethoxy (carbonyl aminophenyl)-N-phenyl carbamate; |
| heterocyclics: | 4-amino-3,5-dichloro-6-fluoro-2-pyridyloxy acetic acid; 4-(1,2-Dimethyl-N-propyl amino)-2-ethyl amino-6-methyl thio-S-triazine; 2-[4,5-dihydro 4-methyl-4-(1-methyl ethyl)-5-oxo-1 H-imidazoyl-2yl-3-pyridinecarboxylic acid; 2-[3,5-dichlorophenyl)-2-(2,2,2-trichloroethyl) oxinane; Butyl-9-hydro-fluorene-(9)-carboxylate; 2-[1-(ethoxy imino) butyl]-3-hydroxy-5-(2H-tetra hydro thio-pyran-3-yl)-2-cyclohexene-ione; 2-(2 chlorophenyl) methyl-4,4-dimethyl-3-iso oxazolidinone; |
| phosphates: | 0-ethyl-0-(3-methyl-6-nitro phenyl) N-sec-butyl phosphoro thio amidate. |

Typical fungicides include (See *Agricultural Chemicals*, Book IV, *Fungicides*, 1989 Revision, W. T. Thomson, Thomson Publications, Fresno, Calif. 93791):

| | |
|---|---|
| organic compounds: | 2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N'-(1,4-piperazinediyl bis (2,2,2-trichloro) ethylidene) bis formamide; Tetramethyl thiuram disulfide; 0-Ethyl-S,S,diphenyl-dithiophosphate; 5,10-dihydro-5,10-dioxo naphtho (2,3,9)-p-dithiin-2,3-dicarbonitrile; 2-(Thiocyano methyl thio) benzothiazole; α-2-(4-chlorophenyl) ethyl]-α- |
| morpholines: | (1,1-dimethyl ethyl)-1H-1,2,4-triazole-1-ethanol; N-tridecyl-2,6-dimethyl morpholine; 4-N-dodecyl-2,6-dimethyl morpholine; |

Typical fumigants, growth regulators, repellants, and rodenticides include (See *Agricultural Chemicals*, Book III, *Fumigants*, 1988–1989 Revision, W. T. Thomson, Thomson Publications, Fresno, Calif. 93791):

| | |
|---|---|
| growth regulants: | 1,2 Dihydro-6-ethyoxy-2,2,4-trimethylquinoline; (2-chloroethyl) phosphoric acid; 4-[acetamino) methyl]-2-chloro-N (2,6-diethyl phenyl acetamide; Benzoic acid, 3,6 dichloro-2-methoxy,2-ethoxy-1-methyl-2-oxo ethyl ester; |
| repellants: | 0,0-dimethyl-0-[(4-methyl thio)-m-tolyl]phosphorothioate; Tetriary butyl-sulfenyl dimethyl dithio carbamate; |
| seed softener: | 2-chloro-6-(trichlomethyl) pyridine; 5-ethoxy-3-trichloromethyl-1,2,4-thiadiazole; N-phenyl-N'-1,2,3-thiadiazol-5-yl urea; |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-trichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (Thanite®),
Ioxynil ester of octanoic acid,
Molinate S-ethyl hexahydro-1H -azepine-1-carbothioate,
PP 511 0,0-dimethyl-(2-diethylamine 4-methyl-6-pyrimidinyl) carbamate,
PP 211 0,0-diethyl 0-(2-diethylamine-4-methyl-6-pyrimidinyl) phosphorocarbamate,
Chlordane 5-Ethoxy-3-(trichlorometyl)-1,2,4-thiadiazole (TERRAZALE®),
Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamatae (TILLAM®),
S-ethyl ethylcyclohexylthiocarbamate (RONEET®),
Malathion (S-(1,2-dicarboxyethyl)-0,0-dimethyl phosphorodithioate),
Diazinon (0,0-diethyl,0-(2-isopropyl-4-methyl-6-pyrimidinyl) phosphorothioate,
O-Ethyl-S-phenyl-ethylphosphonodithioate (DYFONATE®),
Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-triazine) Simazine (2-chloro-4,6,-bis (ethylamino)-s-triazine
Dodine (n-dodecylguanidine acetate)
Thiram (tetramethylthiuram disulfide)
N-(mercaptomethyl)phthalimide s-(o,o dimethylphosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Methoxychlor: 2,2,-Bis(p-methoxyphenyl)-1,1,1-trichloroethane
PP 781:4 (2-chloro phenylhydrazono)-3-methyl-5-isoxazolone*
PP 675:5-butyl-2-dimethylamino-4-hydroxy-6-methyl pyrimidine*
PP 062:5,6-dimethyl-2-dimethylamino-4 pyrimidinyl dimethylcarbamate*
PP 149:5-n-butyl-2 ethylamino-4-hydroxy-6 methyl pyrimidine*

* Manufactured by Imperial Chemical Industries Limited

C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4 -dichlorophenyl)-N', N'-dimethylurea
Neburon N-butyl-N'-( 3,4-dichlorophenyl-N-methylurea
NIA 11092 1,1-dimethyl-3-[3-(n-t-butyl carbamyloxy)phenyl] urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-valerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl) acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzine
1-(butile carbamoyl)-2-benzimidazol carbamic acid, methyl ester (BENLATE®)]

| COMPOSITION OF STABLE, EMULSIFIABLE GEL MATRIX AND CONCENTRATE | | |
| --- | --- | --- |
| Component | Matrix | Concentrate (%) |
| (a) Surfactant | 3–25 | 0.6–20 |
| (b) Solvent System | 70–80 | 10–70 |
| (c) Thickening Agent | 0.3–1.5 | 0.1–1.2 |

-continued

COMPOSITION OF STABLE, EMULSIFIABLE GEL MATRIX AND CONCENTRATE

| Component | Matrix | Concentrate (%) |
|---|---|---|
| (d) Viscosity Enhancer/ Disintegration Aid | 1-3 | 0.2-2.5 |
| (e) Polyhydric Alcohol | 0-6 | 0-5 |
| (f) Organic Diluent | 0-15 | 0-10 |
| (g) Agriculturally Active Chemical | — | 20-80 |
| $\eta$ Cps | 700-10,000 | 5,000-20,000 |
| # of Inversions to disperse in 1:50 in water | <100 | <200 |

EXAMPLES OF STABLE, EMULSIFIABLE GEL CONCENTRATES OF INVENTION

| Component | 1 | 2 | 3 | 4 | 5 | 6 | 7 |
|---|---|---|---|---|---|---|---|
| (a) Surfactant | | | | | | | |
| Gafac ® RE-610 (ISP) | 4.7 | 8.6 | 4.7 | 8.7 | 8.7 | 8.9 | 8.9 |
| (b) Solvent System | | | | | | | |
| N-Methylpyrrolidone | 20.8 | 20.1 | 20.8 | 20.2 | 20.2 | 20.7 | 20.7 |
| N-Octylpyrrolidone | 20.8 | 10.1 | 20.8 | 10.1 | 10.2 | 10.3 | 10.3 |
| (c) Thickening Agent | | | | | | | |
| Hydroxy Propyl Cellulose | 0.25 | 0.5 | 0.25 | 0.35 | 0.25 | 0.25 | 0.25 |
| (d) Viscosity Enhancer/ Disintegration Aid | | | | | | | |
| Ganex ® P 904 | 1.0 | 1.0 | 1.0 | 1.0 | 1.0 | 1.0 | — |
| PVP K-120 | — | — | — | — | — | — | 1.0 |
| (e) Polyhydric Alcohol | | | | | | | |
| Glycerol | 2.5 | 2.5 | 2.5 | 2.5 | 2.5 | 1.5 | 1.5 |
| (f) Organic Diluent | | | | | | | |
| Exxon Aro 200 | 0 | 7.2 | 0 | 7.2 | 7.2 | 7.4 | 7.4 |
| (g) Agriculturally Active Chemical | | | | | | | |
| Atrazine | (20.5) | 50 | 50 | 50 | 50 | 50 | 50 |
| Aatrax ® (Ciba-Geigy) | 50 | — | — | — | — | — | — |
| Total | 100 | 100 | 100 | 100 | 100 | 100 | 100 |
| $\eta$ cps >5000 | | | | | | | |

The above concentrates were stable gels with the appearance of a thick paste.

When diluted with water at a concentration of 0.8-1.0 g. in 50 g. of water, stable, uniform dispersions were produced upon rapid disintegration, e.g. within 14-76 inversions. The quality of the dispersions were comparable to commercial Aatrax ® (Ciba-Geigy) flowable agricultural compositions after standing for 1½ to 2½ hours.

What is claimed is:

1. A stable, emulsifiable gel matrix for forming an emulsifiable gel concentrate upon addition of an agriculturally active chemical which, upon dilution with water, will disintegrate rapidly and form a uniform dispersion at high chemical loading, comprising, by weight of the matrix:
   (a) 3-25% of an anionic or nonionic surfactant,
   (b) 70-80% of a solvent system composed of first and second lactam components to solubilize and disperse the chemical, wherein the first component is a $C_1$-$C_4$ alkylpyrrolidone and the second component is a $C_6$-$C_{18}$ alkylpyrrolidone,
   (c) 0.3-1.5% of a hydroxyalkyl cellulose thickening agent,
   (d) 1-3% of a high molecular weight polymer selected from the group consisting of polyvinylpyrrolidone, a vinylpyrrolidone copolymer, and a half-ester of maleic anhydride-alkyl vinyl ether copolymer, to provide a viscosity enhancer, or disintegration aid, or both, function for the matrix, and
   (e) optionally including 0-6% of a polyhydric alcohol or
   (f) 0-15% of an organic diluent selected from the group consisting of soybean oil, rapeseed oil, long chain alcohols, long chain ketones, long chain esters, which have 6 or more carbon atoms, and ethers, or both.

2. A gel matrix according to claim 1 wherein: the viscosity is about 700-10,000 cps and the number of inversions to disperse the gel in a 1:50 ratio in water is <100.

3. A stable, emulsifiable gel concentrate comprising: the gel matrix of claim 2, and (g) an agriculturally active chemical.

4. A gel matrix according to claim 1 wherein:
   (e) has at least 3 hydroxyl groups, and
   (f) is an aromatic organic oil.

5. A stable, emulsifiable gel concentrate comprising: the gel matrix of claim 4 and (g) an agriculturally active chemical.

6. A gel matrix according to claim 1 wherein:
   (a) is a nonylphenol ethoxylated phosphate ester,
   (b) comprises N-methylpyrrolidone and N-octylpyrrolidone,
   (c) is hydroxy propyl cellulose,
   (d) is polyvinylpyrrolidone K-120, a copolymer of vinylpyrrolidone and an alkene, or mixtures thereof,
   (e) is glycerol, and
   (f) includes naphtha and other aromatic oils.

7. A gel concentrate comprising: the gel matrix of claim 6, and (g) an agriculturally active chemical.

8. A stable, emulsifiable gel concentrate comprising: the gel matrix of claim 1, and (g) an agriculturally active chemical.

9. The gel concentrate of claim 8 wherein:
   (a) is 0.6-20%,
   (b) is 10-70%, (c) is 0.1–1.2%,
(d) is 0.2–2.5%,
(e) is 0–5%,
(f) is 0–10%, and
(g) is 20–80%.

10. A stable, aqueous macroemulsion comprising: the gel concentrate of claim 8, and dilution water.

11. An aqueous macroemulsion comprising: the gel concentrate of claim 8, and at least 1:50 of dilution water.

* * * * *